United States Patent
Pinchuk et al.

(10) Patent No.: US 11,911,572 B2
(45) Date of Patent: Feb. 27, 2024

(54) SOFT TIP DRUG-ELUTING URINARY DRAINAGE CATHETER

(71) Applicant: InnoCare Urologics, LLC, Miami, FL (US)

(72) Inventors: Leonard Pinchuk, Miami, FL (US); Bryan Pinchuk, Miami, FL (US); Gary A. Kalser, Winter Park, FL (US)

(73) Assignee: InnoCare Urologics, LLC, Miami, FL (US)

( * ) Notice: Subject to any disclaimer, the term of this patent is extended or adjusted under 35 U.S.C. 154(b) by 0 days.

(21) Appl. No.: 17/737,697

(22) Filed: May 5, 2022

(65) Prior Publication Data
US 2023/0355924 A1    Nov. 9, 2023

(51) Int. Cl.
*A61M 25/00*    (2006.01)
*A61M 25/10*    (2013.01)

(52) U.S. Cl.
CPC ...... *A61M 25/0074* (2013.01); *A61M 25/001* (2013.01); *A61M 25/0017* (2013.01); *A61M 25/10* (2013.01)

(58) Field of Classification Search
CPC .. A61M 2025/0065; A61M 2025/0081; A61M 25/0068; A61M 25/0069; A61M 27/008; A61M 25/0009; A61M 25/001; A61M 25/0017; A61M 25/0054; A61M 25/0074; A61M 25/10; A61B 2017/00004; A61L 27/56; A61L 29/145; A61L 29/148; A61L 31/145
See application file for complete search history.

(56) References Cited

U.S. PATENT DOCUMENTS

| | | | | |
|---|---|---|---|---|
| 3,566,874 A | * | 3/1971 | Shepherd | A61M 25/0009 424/422 |
| 3,695,921 A | * | 10/1972 | Shepherd et al. | A61L 29/041 427/2.3 |
| 3,736,939 A | | 6/1973 | Taylor | |
| 4,055,682 A | * | 10/1977 | Merrill | C08L 39/06 427/2.3 |
| 4,657,544 A | * | 4/1987 | Pinchuk | C08J 9/26 623/1.39 |
| 4,759,757 A | | 7/1988 | Pinchuk | |

(Continued)

FOREIGN PATENT DOCUMENTS

| | | |
|---|---|---|
| WO | 2007005734 A2 | 1/2007 |
| WO | 2016107719 A1 | 7/2016 |

OTHER PUBLICATIONS

Elute Definition & Meaning | Dictionary.com. https://www.dictionary.com/browse/elute. Accessed Jul. 10, 2023.*

(Continued)

*Primary Examiner* — Adam Marcetich
(74) *Attorney, Agent, or Firm* — Gordon & Jacobson, P.C.

(57) ABSTRACT

A balloon retention urinary catheter includes a porous and spongy distal tip. In one method, a polymer is mixed with sacrificial particles and the mixture is molded in the form of the tip, and then cured. The cured tip is then placed in a solvent in which the sacrificial particles elute from the tip but in which the polymer is insoluble. Once the particles elute out of the polymer in the tip, a softer porous polymeric structure results. The tip may be structured to be softer prior to use or for transformation to a softer state once in the bladder.

18 Claims, 5 Drawing Sheets

(56) References Cited

U.S. PATENT DOCUMENTS

| | | | | |
|---|---|---|---|---|
| 4,773,901 | A | * | 9/1988 | Norton .................. A61L 29/085 604/265 |
| 4,905,367 | A | * | 3/1990 | Pinchuk .................. A61L 17/04 29/458 |
| 5,049,138 | A | | 9/1991 | Chevalier et al. |
| 5,266,669 | A | * | 11/1993 | Onwunaka .............. A61L 29/06 528/78 |
| 6,184,266 | B1 | | 2/2001 | Ronan et al. |
| 6,652,581 | B1 | * | 11/2003 | Ding ........................ A61L 31/16 623/1.45 |
| 8,070,718 | B2 | | 12/2011 | Weber et al. |
| 2002/0138154 | A1 | * | 9/2002 | Li ............................. A61L 29/16 424/428 |
| 2004/0122464 | A1 | | 6/2004 | Wang et al. |
| 2006/0051393 | A1 | * | 3/2006 | Heruth .................... A61L 27/54 427/2.24 |
| 2006/0088567 | A1 | * | 4/2006 | Warner ................... A61L 27/54 427/2.26 |
| 2006/0136071 | A1 | * | 6/2006 | Maspero ............. A61L 27/3847 623/23.76 |
| 2009/0246252 | A1 | * | 10/2009 | Arps ..................... A61L 29/041 424/425 |
| 2010/0261662 | A1 | | 10/2010 | Schreck et al. |
| 2010/0282394 | A1 | | 11/2010 | Watson |
| 2015/0141900 | A1 | * | 5/2015 | Kalloo .............. A61M 25/0082 604/14 |
| 2015/0367099 | A9 | | 12/2015 | Pinchuk et al. |
| 2016/0184551 | A1 | | 6/2016 | Nyman et al. |
| 2020/0230295 | A1 | * | 7/2020 | Mannarino ........... A61L 29/041 |

OTHER PUBLICATIONS

Elute Definition & Meaning—Merriam-Webster. https://www.merriam-webster.com/dictionary/elute. Accessed Jul. 10, 2023.*
"A Novel Device-Integrated Drug Delivery System for Local Inhibition or Urinary Tract Infection", Staerk et al., Frontiers in Microbiology, Jun. 2021, vol. 12, Article 685698.
"A Preliminary Evaluation of Ovine Bladder Mucosal Damage Associated With 2 Different Indwelling Urinary Catheters," Greenberg et al., Technology and Engineering, vol. 110, pp. 248-252, 2017.
"Coated Urinary Catheter by PEG/PVA/gentamicin with Drug Delivery Capability Against Hospital Infection", Rafienia et al., Iranian Polymer Journal 22, 75-83 (2013).
"Co-release of Dicloxacillin and Thioridazine from Catheter Material Containing an Interpenetrating Polymer Network for Inhibiting Device-Associated *Staphylococcus aureus Infection*", Stenger et al., Science Direct, vol. 241, Nov. 10, 2016, pp. 125-134.
"Indwelling Urinary Catheter Assembled with Lidocaine-Loaded Polymeric Strand for Local Sustained Alleviation of Bladder Discomfort", Cho Rim Kim et al., Bioengineering & Translational Medicine, 2021;6:e10218.
Urinary Catheter Coating Modifications: The Race Against Catheter-Associated Infections, Andersen et al., Coatings 2020, 10, 23; doi:10.3390/coatings10010023.
PCT Search Report and Written Opinion dated Oct. 18, 2023 of Application No. PCT/US2023/021134.

* cited by examiner

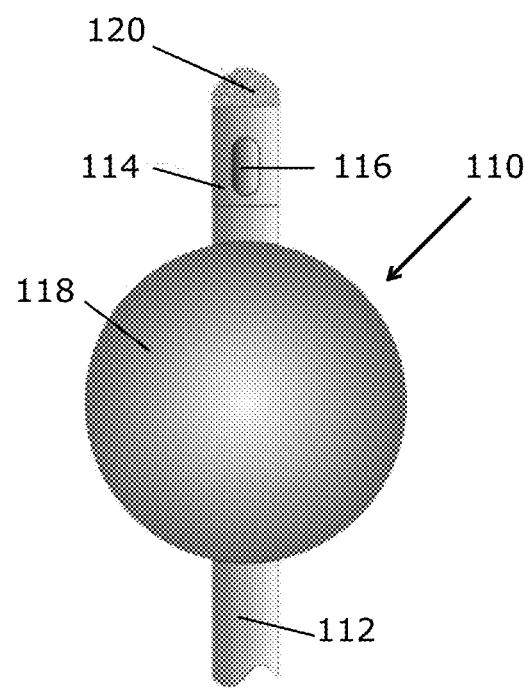
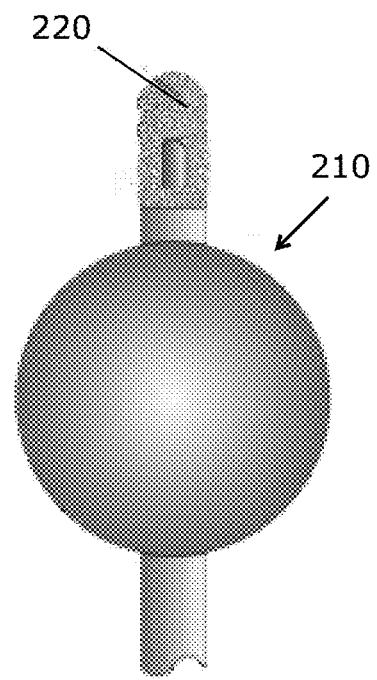
FIG. 5
FIG. 10
FIG. 11

SOFT TIP DRUG-ELUTING URINARY DRAINAGE CATHETER

BACKGROUND OF THE INVENTION

1. Field of the Invention

The following description relates to medical devices. More particularly, the following description relates to catheters, and more specifically balloon catheters adapted as urinary drainage catheters.

2. State of the Art

Annually, millions of individuals require balloon retention urinary catheters, referred to as Foley catheters, for temporary or chronic urinary drainage management. Referring to Prior Art FIGS. 1 and 2, a prior art Foley catheter 10 includes a catheter shaft 12 having a first lumen extending to a distal end 14 and opening to a drainage port 16, and a second lumen extending to a retention balloon 18. The distal end 14 of the catheter shaft 12 has a distal tip 20 which may be unitary with the catheter shaft 12 or attached by adhesion or other bonding. The proximal end 13 of the catheter is provided with a hub 24 having first and second ports 26, 28 adapted to respectively couple the first lumen to a drainage bag and the second lumen to a syringe with an inflation fluid. The distal tip 20 has an ostensibly atraumatic rounded end 22. Turning to Prior Art FIG. 3, in use, the Foley catheter is tracked along the urethra 30 until the retention balloon 18 is passed into the patient's bladder 32. the retention balloon 18 is then inflated via the second lumen with a fluid supplied by the syringe until the desired volume of fluid has filled the balloon, typically 10 cc to 30 cc.

The distal tip 20 of the catheter serves as the leading end during tracking through the urethra. If the tip is too rigid, it would be difficult to navigate the catheter through the bends in the male urethra and the tip could perforate the wall of the urethra when traversing an acute bend or an enlarged prostate gland. On the other hand, if the distal tip 20 is too soft, the catheter can deform back on itself when maneuvering through areas around a swollen prostate, which is common in older patients.

In addition, once the distal tip enters the bladder, it is deleterious to the patient for the distal tip to be as rigid as desirable when tracking through the urethra. Referring to Prior Art FIG. 4, when the bladder 32 empties, the rigid distal tip 20 contacts the bladder dome 34, thereby 'tenting' the bladder dome and creating a single direct contact point which can irritate the bladder tissue. This constant contact has been studied and published in the literature and is well-known to cause irritation and inflammation which has been shown to cause bladder and urinary tract infections, a leading cause of morbidity and mortality in the hospital setting. Further, if the distal tip perforates the bladder, more serious complications can occur including septicemia and death.

Several approaches have been studied to counteract such deleterious effects, including a pancake balloon with flat tip, and a dual balloon Foley catheter. The pancake balloon with flat tip is short in length and is intended to reduce contact between the catheter tip and the bladder wall once the catheter is in place. The problem with the flat tip design is that it has a shorter length available for tracking and thus presents an increased risk of irritating and damaging the sensitive walls of the urethra as the catheter is advanced through the urinary tract to the bladder. The dual balloon Foley catheter design uses a first balloon to retain the catheter in the bladder and a second balloon at the distal tip to serve as a cushion to prevent trauma to the bladder wall. The problem with two balloons is that the catheter requires the two balloons and two inflation mechanisms, both of which are costly. In addition, the care staff must attend to two separate inflations which are bothersome, must be managed properly, and are time-consuming to operate.

Another frequent problem associated with Foley catheters is the large instances of infection and encrustation of the catheter. One study estimates that up to 50% of long-term indwelling urinary catheters will become blocked or encrusted, reducing or preventing urine drainage through the catheter. As bacteria grows over time, urease is produced, which cleaves uric acid leading to ammonium and carbon dioxide. The normal pH range of urine is 4.5 to 8.0; however, the presence of ammonium can increase the alkalinity of the urine to a pH as high as 11. As the urine becomes alkaline, crystallization of magnesium and calcium phosphates from the urine is induced. In addition, bacteria colonize the catheter surfaces forming a bacterial biofilm. The crystalline material aggregates in the urine and in the bacterial biofilm and can result in deposits which eventually block the flow of urine through the catheter.

A blocked or encrusted catheter can lead to problematic downstream effects. These include reflux of urine to the kidney, septicemia, pyelonephritis, and endotoxic shock. Managing the nucleation pH of the urine has been identified as a possible way to curb and manage blockage and subsequent bladder stone formation. Blockage has been seen in some studies to occur as early as two days after catheterization.

SUMMARY OF THE INVENTION

Balloon retention urinary catheters and components therefor are provided which address various shortcomings of prior art Foley catheters. In an embodiment, a balloon retention urinary catheter includes a catheter shaft having a first lumen extending from a proximal end to a distal end and opening to a drainage port, and a second lumen extending to a retention balloon. The proximal end of the catheter is provided with a hub having first and second ports adapted to respectively couple the first lumen to a drainage bag and second lumen to a syringe with an inflation fluid. The distal end of the catheter shaft is provided with a distal tip which can optionally have a hole located in-line with the catheter shaft and extending through the distal tip. The distal tip is porous and spongy and presents as soft and atraumatic. The distal tip can be integrally formed with the end of the catheter shaft or formed as a separate cap and adhered to the distal end of the catheter shaft, e.g., by a suitable bonding agent. In one preferred method of manufacture, a polymer is mixed with sacrificial particles and the mixture is molded in the form of the tip, and then cured. The cured tip is then placed in a solvent in which the sacrificial particles elute from the tip but in which the polymer is insoluble. Once the particles elute out of the polymer in the tip, a softer porous polymeric structure results.

In yet another embodiment, a balloon retention urinary catheter is provided with a distal tip that changes structural characteristics after it is received in the bladder. The distal tip is semi-rigid in an initial structural configuration which is advantageous in maneuvering through the urethra and into the bladder. Once in the bladder, the distal tip automatically changes to a softer, more flexible configuration to prevent irritation of the bladder wall. To effect the change in hardness and flexibility, a preferred method of manufacture includes making the tip from a combination of a polymer and particles that will elute from the polymer in the bladder environment. Then, once in the bladder, the particles elute out of the polymer, leaving a softer porous polymeric structure.

In another embodiment, a balloon retention urinary catheter is provided with a distal tip that is similar to the previously described embodiment, but which is designed to elute particles having a therapeutic effect in the bladder. In order for there to be a therapeutic effect, the eluted particle may or may not constitute a drug. Such distal tip is preferably also adapted to become softer and more flexible as the particles are eluted from the distal tip of the balloon retention urinary catheter.

In another embodiment, a distal tip in the form of a cap is provided for attachment to a standard Foley catheter. The cap is preferably 1 to 3 mm thick and is adapted to cover the distal tip of a conventional Foley catheter. The cap can have any of the structural and therapeutic advantages of the embodiments described above. That is, in one embodiment, the cap can be manufactured to have a soft spongy structure that is adapted to present an atraumatic leading end to a standard Foley catheter to thereby prevent irritation of the bladder wall without significantly changing the tracking characteristics of the tip of the standard Foley catheter. In another embodiment, the cap can be manufactured to be rigid during tracking and advancement into to the bladder, but then elute particles in the presence of urinary fluid to form a softer spongy structure that is atraumatic to the bladder wall. In yet another embodiment, the cap can be manufactured to be rigid during tracking into the bladder, but then elute particles in the bladder that have a therapeutic effect and optionally also which result in the distal tip having softer spongy structure that is atraumatic to the bladder wall.

BRIEF DESCRIPTION OF THE DRAWINGS

Prior Art

Prior Art

Prior Art

Prior Art

FIG. 5 shows a distal end of balloon retention urinary catheter with a soft tip provided thereto according to an embodiment herein.

FIG. 10 shows a distal end of balloon retention urinary catheter according to embodiments herein.

FIG. 11 shows a separate cap for fitting to a conventional balloon retention urinary catheter.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use, and specifically intended to be located within the bladder.

Figure 1:
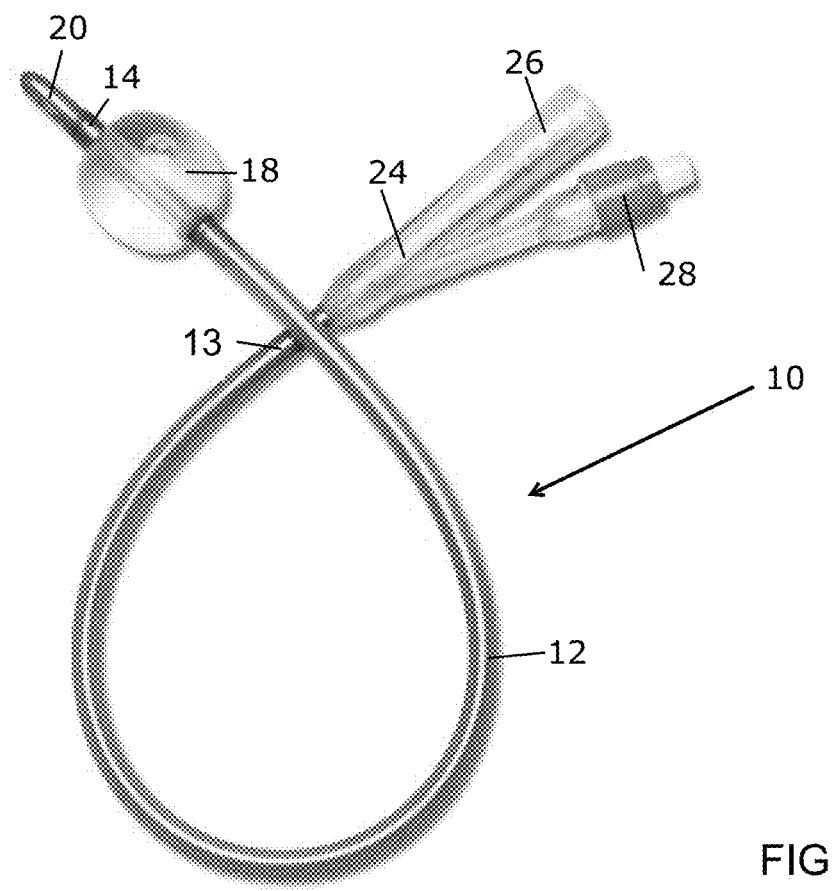
FIG. 1 is a prior art balloon retention urinary catheter.
Figure 2:
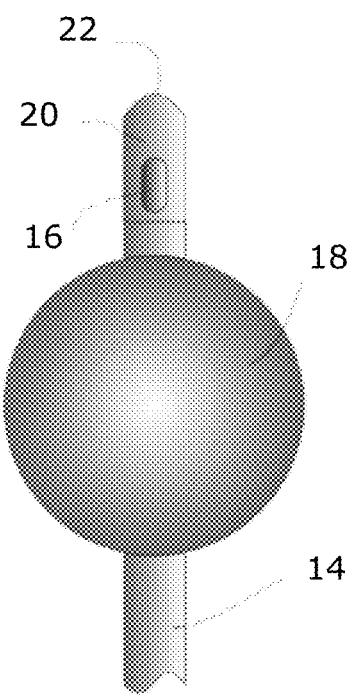
FIG. 2 is an enlarged distal end of the prior art balloon retention urinary catheter of Prior Art FIG. 1.
Figure 3:
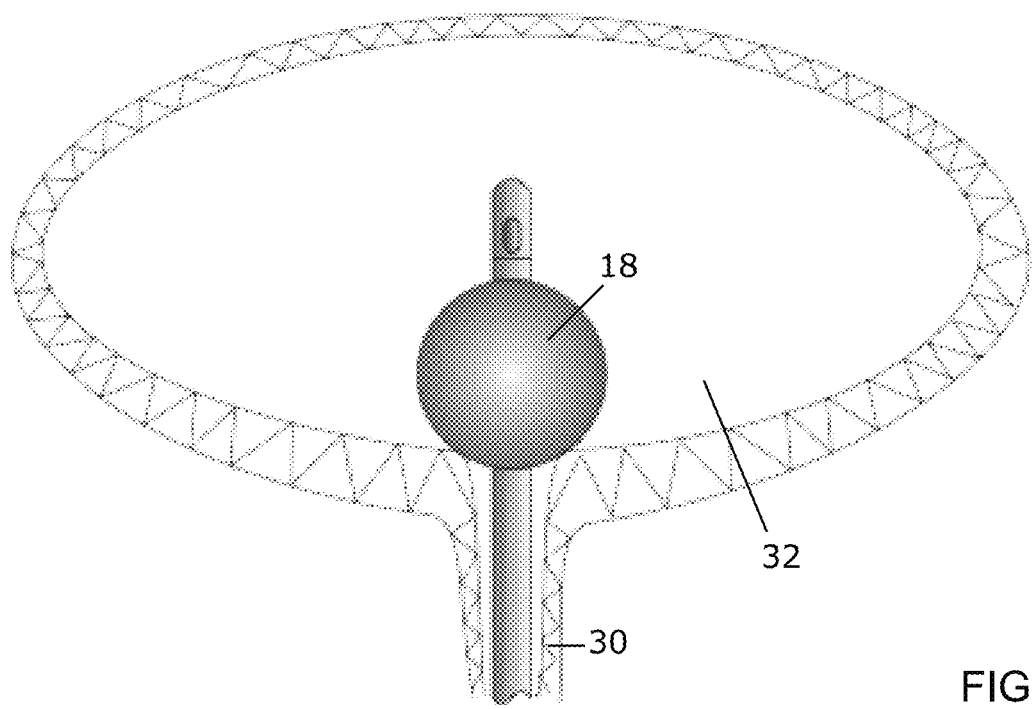
FIG. 3 illustrates a prior art balloon retention urinary catheter inserted into the bladder when the bladder is full of urinary fluid.
Figure 4:
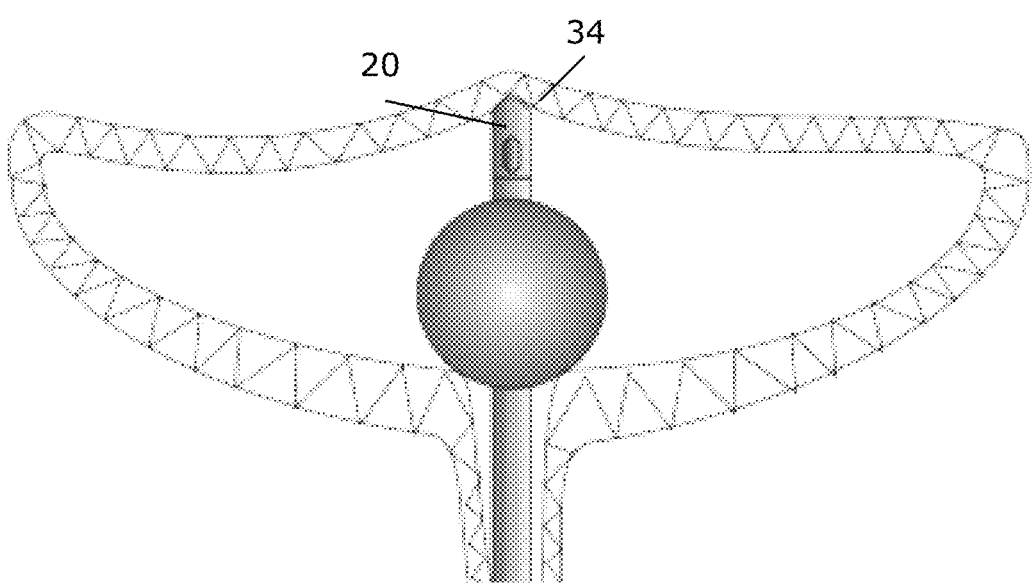
FIG. 4 illustrates a prior art balloon retention urinary catheter inserted into the bladder that is sufficiently empty of urinary fluid such that the bladder dome contacts the distal tip of the prior art balloon retention urinary catheter.

Referring to FIG. 5, the distal end of a balloon retention urinary catheter according to an embodiment hereof is shown. The balloon retention urinary catheter 110 includes a catheter shaft 112 having a first lumen extending along the catheter shaft from a proximal end (not shown, but similar to proximal end 13 in FIG. 1) to a distal end 114 and opening to a drainage port 116, and a second lumen extending to a retention balloon 118. As described with respect to the prior art conventional balloon retention urinary catheter (FIG. 1), the proximal end of the catheter shaft 112 is provided with a hub having first and second ports adapted to respectively couple the first lumen to a drainage bag and the second lumen to a syringe with an inflation fluid. In accord with an aspect of the embodiment described herein, the distal end 114 of the catheter shaft is provided with a porous, spongy distal tip 120. The distal tip 120 can be integrally formed with the end of the catheter shaft, or formed as a separate cap and adhered to the distal end of the catheter shaft, e.g., by a suitable bonding agent. The distal tip 120 optionally can have a hole (not shown) located in-line with the catheter shaft and extending through the distal tip.

The catheter shaft 112, retention balloon 116, and distal tip 120 can be made from any polymeric material commonly used in the manufacture of catheters. Exemplary materials include but are not limited to silicone rubber, polyurethane, polyolefins, fluorinated polymer, nylons, amorphous nylons, polyesters, amorphous polyesters, and combinations of the above.

The porous spongy distal tip 120 is very soft relative to the catheter shaft 112 and atraumatic. In compressibility measurements, discussed below, the spongy distal tip is 20 to 50% more compressible that the same polymer in a non-spongy form. In an embodiment, the distal tip 120 is made combining a polymer and a sacrificial component, preferably in the form of elutable particles, and then removing the sacrificial component to leave behind pores in the polymer. The polymer can be the same polymer used in the manufacture of the catheter 112 and/or the balloon 118 or a different polymer. The sacrificial component are preferably particles which can be eluted into a solvent, such as a salt. Exemplary sacrificial component particles include, but are not limited, to sodium chloride, potassium chloride, potassium citrate, sodium citrate, sodium bicarbonate, sodium carbonate, carbonic acid, phosphate buffer powder, potassium phosphate, bismuth subsalicylate, acetylsalicylic acid, salicylic acid, citric acid, sugar, protein, carbohydrates, flour, soluble polymers (polyethylene oxide), as well as anhydrous versions of the above and combinations of the above. Preferred criteria for the sacrificial component is that the particles of the sacrificial component elute from around the polymer when in the solvent and that the particles do not leave behind a toxic residue. The particles are loaded in the polymer at between 10% to 95% weight of particle to polymer. A preferred ratio is 60% to 70% particles, by weight to polymer, dispersed in the polymer. The solvent can be water or any other solvent in which the polymer is insoluble.

In one method of manufacture, the sacrificial component is combined with the polymer into a heterogenous mixture while the polymer is in a melt phase. Then, the heterogenous mixture is molded in the form of the distal tip and cured. The distal tip 120 can be molded directly onto the distal end 114 of the catheter shaft 112, or can be molded as a separate component for later attachment to the catheter shaft. After the distal tip 120 is molded and cured, the distal tip is placed into an appropriate solvent into which the sacrificial component is soluble, and the polymer is insoluble. The distal tip 120 is left in the solution until at least some and preferably substantially all of the sacrificial component has eluted into the solvent. Preferably at least 50% of the sacrificial component, and up to 100% of the sacrificial component elutes into the solvent, resulting in pores from where the sacrificial component has eluted.

In one exemplar embodiment, the sacrificial component comprises a combination of equal parts sodium bicarbonate and anhydrous citric acid in a heterogenous mixture with silicone polymer. The particulate sacrificial component is 70% by weight, and the silicone polymer is 30% by weight in the heterogenous mixture. This mixture is molded and cured in the shape of the distal tip. When the cured distal tip is placed into a solution of water, a bubbling action occurs as the sacrificial component elutes, which concomitantly serve as an indicator of when the elution is complete; i.e., when the bubbling stops. After the bubbling stops, the distal tip is substantially all silicone, with a porous spongy structure. The spongy distal tip is preferably 1 to 3 mm thick at the distalmost end and can serve as a cushion against tissue. The tip is bonded to the distal end of the balloon retention urinary catheter.

Figure 6:
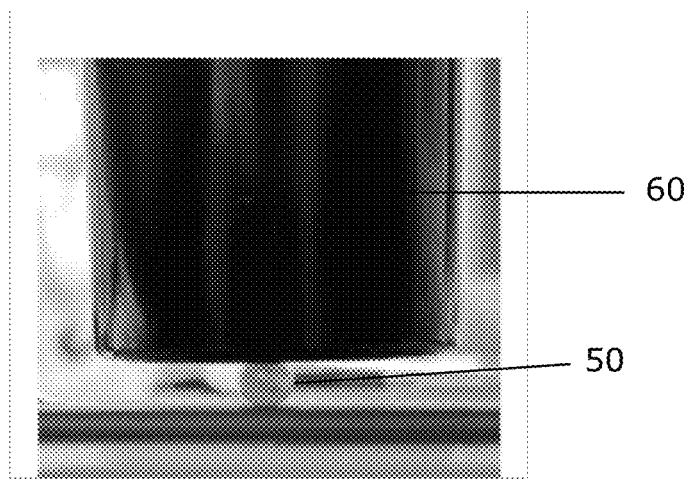
FIG. 6 shows the deformation behavior of a prior art balloon retention urinary catheter subject to deformation from a 500 g weight.
Figure 7:
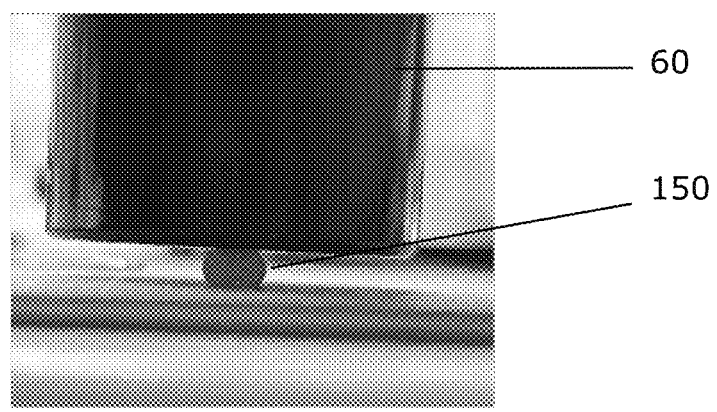
FIG. 7 shows the deformation behavior of a balloon retention urinary catheter described herein subject to deformation from a 500 g weight prior to soaking in water.
Figure 8:
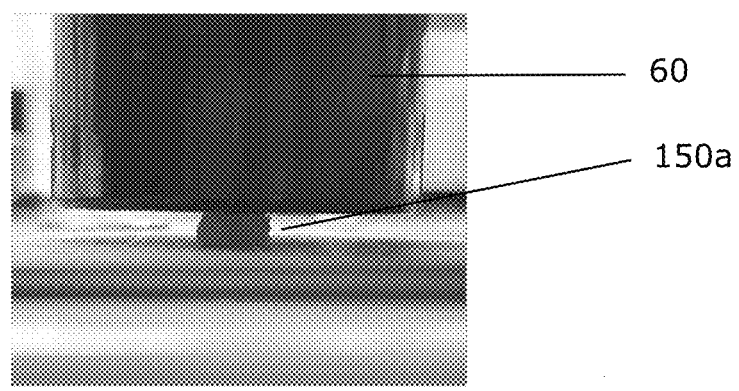
FIG. 8 shows the deformation behavior of a balloon retention urinary catheter described herein subject to deformation from a 500 g weight after soaking in water for 20 minutes.
Figure 9:
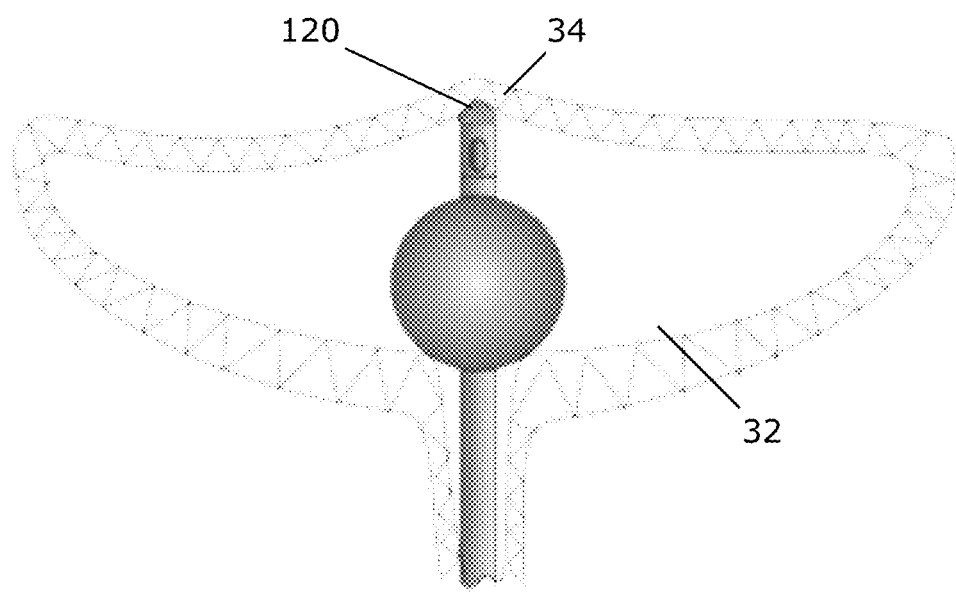
FIG. 9 illustrates an embodiment of a balloon retention urinary catheter inserted into the bladder that is sufficiently empty of urinary fluid.

Turning now to FIGS. 6 through 8, a comparison of the sponginess of the material of the distal tip described herein relative to the conventional material is shown. FIG. 6 shows the compressibility of a piece of silicone rubber material 50 used to manufacture the distal end of a conventional balloon retention urinary catheter when subject to deformation by a 500 g weight 60. FIG. 7 shows the deformation behavior of the porous material 150 described herein used for the distal tip of the balloon retention urinary catheter when subject to deformation from the 500 g weight 60 prior to soaking in water; and FIG. 8 shows the deformation behavior of that same porous material 150a after soaking in water for 20 minutes. It can be seen that a distal tip made from the material described herein is significantly more compressible (approximately 25%), particularly after being in the environment of fluid in a bladder. Turning to FIG. 9, the resulting porous structure of the distal tip 120 is compressible, has a reduced hardness, and is atraumatic to the inner wall 34 of the bladder 32. As such, the balloon retention urinary catheter has a soft and atraumatic distal end without the disadvantages of a pancake balloon or a second balloon.

Referring to FIG. 10, in another embodiment, a balloon retention urinary catheter 210, substantially as described above, is provided with a distal tip 220 that changes structural characteristics after it is fully manufactured and once it is received in the bladder. The distal tip 220 as formed is semi-rigid in an initial structural configuration which is advantageous in maneuvering the distal end of the catheter through the urethra and into the bladder. The tip may be molded and cured in the same manner as the prior embodiment; however, the eluting particles are retained in the tip until after delivery into the bladder. The eluting particles can be any particles that are capable and safe to elute in the urinary fluid. Thus, the particles may be many of the same particles described above. In addition, the particles can be those that can serve as a buffer in the urine to maintain the pH of urine in a desired pH range of 6 to 8. As such, the eluting particles can provide a therapeutic effect. By way of example, sodium phosphate and sodium chloride can both be used as eluting particles from the distal tip.

When eluted into water or urine, such particles form phosphate buffered saline. A phosphate buffer system can be made with phosphoric acid ($H_3PO_4$) in equilibrium with dihydrogen phosphate ion ($H_2PO_4^-$) and $H^+$ The pK for this phosphate buffer is 6.8, which allows this buffer to function within its optimal buffering range at physiological pH. By way of another example, potassium chloride and potassium phosphate can be used in combination as eluting particles. As the particles elute out of the tip, the particles can bring the pH of urine into a preferred range of pH 6 to 8 and prevent the crystallization of minerals and formation of encrustations. In addition, eluting particles can include select proteins, such as histidine.

In an exemplar embodiment, potassium citrate is mixed into silicone at a weight ratio of 70% potassium citrate to 30% silicone. Once the particles are dispersed in the polymer, the mixture is provided into a mold to form the shaft of the catheter tip and allowed to cure. The cured tip is then bonded to the silicone catheter using an adhesive agent and allowed to dry. The adhesive agent can be a room temperature vulcanizing silicone adhesive.

The distal tip 220 as formed is sufficiently stiff to provide suitable tracking through the urethra to the urinary bladder where the potassium citrate dissolves out, increases the pH of the urine in the bladder and reduces encrustations. The tip becomes soft and non-irritating to the bladder wall thereby reducing urinary tract infections.

In another embodiment, a balloon retention urinary catheter is provided with a distal tip that is similar to the previously described embodiment, but which further designed to elute particles in the bladder that have a therapeutic effect in the bladder. It is appreciated that for there to be a therapeutic effect, the eluted particle may or may not be construed as a drug. Such distal tip is preferably also adapted to become softer and more flexible as the particles are eluted from the distal tip of the balloon retention urinary catheters catheter.

By way of example, a therapeutically effective particle includes potassium citrate, which can increase the pH of urine if otherwise too low. By way of another example, the therapeutically effective particles include citric acid, which can decrease the pH of urine if the pH is too high. This loading can be within the catheter body 11 surface or just within the distal tip 13 or combinations thereof. Loading particulate into the catheter body surface can be effectuated by rolling the catheter, silicone in this example, in a non-cured silicone media, such as silicone caulking, and then pressing the particulate into the media now located on the catheter body and then curing. As the catheter dwells within the bladder, the soluble agent elutes out of the polymer leading to regulation of pH as well as reducing the stiffness of the distal tip material. Other therapeutically effective particles can also include antibiotics, antifibrotics, antimicrobials, anti-inflammatories, and antispasmodics (anticholinergics), alone, in combination with each other, or in combination with any of the previously described soluable agents. Exemplary soluble antibiotics include, but are not limited to, amoxicillin, ampicillin, ceftriaxone (Rocephin), cephalexin (Keflex), ciprofloxacin, doxycycline, fosfomycin (Monurol), levofloxacin (Levaquin), methenamine (Hiprex), nitrofurantoin (Macrobid, Macrodantin), trimethoprim/sulfamethoxazole (Bactrim), and similar agents. Exemplary antifibrotics include, but are not limited to, Paclitaxel, Mitomycin C, Rapamycin, and the analogs of these and similar drugs. Exemplary antimicrobials include, but are not limited to, oligodynamic metals such as copper ion, zinc ion, silver ion with their associated counterions (chloride, bromide, iodide, hydroxide, etc.), quaternary ammonium salts, and the like. Exemplar anti-inflammatories include, but are not limited to, aspirin and ibuprofen. An exemplar antispasmodic (anticholinergic) agent includes oxybutynin.

Turning now to FIG. 11, in other embodiments, caps 300 are provided for attachment to conventional urinary balloon retention catheters. The caps 300 are manufactured in the same manner as the any of the above described distal tips; i.e., to be in the form of a soft, porous, atraumatic material upon manufacture, or with sacrificial particles that cause the tip to become more flexible (spongy) after insertion into the bladder, and/or with therapeutic eluting particles. Thus, the advantages of any of the preceding catheters can be applied to conventional urinary balloon retention catheters by securing the cap to the distal end thereof. The cap may be secured by form fit, interference fit, by gluing or other adhesion, or by any other suitable means.

There have been described and illustrated herein embodiments of balloon retention urinary catheters, components therefor, and methods of manufacturing such catheters and components. While particular embodiments of the invention have been described, it is not intended that the invention be limited thereto, as it is intended that the invention be as broad in scope as the art will allow and that the specification be read likewise. Thus, while particular description has been provided in reference to a using silicone in the construction of the distal tip for the balloon retention urinary catheter, other polymers suitable for construction of a such a catheter can similarly be used in the manufacture of a soft, spongy tip which may or may not elute a therapeutic agent and are hereby described as being suitable in such manufacture. It will therefore be appreciated by those skilled in the art that yet other modifications could be made to the provided invention without deviating from its scope as claimed.

What is claimed is:

1. A balloon retention urinary catheter for insertion into a bladder of a patient, comprising:
    a) an elongate catheter shaft extending between a proximal end and a distal end;
    b) a balloon adjacent the distal end;
    c) a drainable port distal of the balloon; and
    d) a distal tip at the distal end, the distal tip including a polymer component that is insoluble in urinary fluid in the bladder and which is combined with an eluting component that is dissolvable by urinary fluid and adapted to elute from the distal tip in the presence of urinary fluid in order to increase flexibility of the distal tip.

2. The balloon retention urinary catheter according to claim 1, wherein the distal tip is adapted to be relatively stiffer prior to introduction into urinary fluid, and more flexible after introduction into urinary fluid.

3. The balloon retention urinary catheter according to claim 1, wherein the distal tip is made by a process of,
    combining the polymer component with the eluting component to form a heterogenous mixture,
    molding the heterogenous mixture in a shape of the distal tip, the eluting component being non-toxic to the patient when eluted in the bladder.

4. The balloon retention urinary catheter according to claim 3, wherein the polymer component is one of silicone, polyurethane, polyolefins, fluorinated polymer, nylons, amorphous nylons, polyesters, amorphous polyesters.

5. The balloon retention urinary catheter according to claim 4, wherein the eluting component includes a salt.

6. The balloon retention urinary catheter according to claim 4, wherein the eluting component includes at least one of sodium chloride, potassium chloride, potassium citrate, sodium citrate, sodium bicarbonate, sodium carbonate, carbonic acid, phosphate buffer powder, potassium phosphate, bismuth subsalicylate, acetylsalicylic acid, salicylic acid, citric acid, sugar, protein, carbohydrates, flour, soluble polymers, and anhydrous versions of any of the preceding.

7. The balloon retention urinary catheter according to claim 1, wherein the eluting component is therapeutically effective when eluted from the distal tip into the bladder.

8. The balloon retention urinary catheter according to claim 7, wherein the eluting component includes at least one of antibiotics, antifibrotics, antimicrobials, anti-inflammatories, and antispasmodics.

9. The balloon retention urinary catheter according to claim 8, wherein the eluting component includes at least one of amoxicillin, ampicillin, ceftriaxone, cephalexin, ciprofloxacin, doxycycline, fosfomycin, levofloxacin, methenamine, nitrofurantoin, and trimethoprim/sulfamethoxazole.

10. The balloon retention urinary catheter according to claim 8, wherein the eluting component includes at least one of Paclitaxel, Mitomycin C, Rapamycin, and analogs thereof.

11. The balloon retention urinary catheter according to claim 8, wherein the eluting component includes at least one of oligodynamic metals such as copper ion, zinc ion, silver ion, and quaternary ammonium salts.

12. The balloon retention urinary catheter according to claim 8, wherein the eluting component includes at least one of aspirin and ibuprofen.

13. The balloon retention urinary catheter according to claim 8, wherein the eluting component includes oxybutynin.

14. The balloon retention urinary catheter according to claim 1, wherein the eluting component is in the form of particles.

15. The balloon retention urinary catheter according to claim 1, wherein the eluting component comprises salt particles.

16. An improved balloon retention urinary catheter, the balloon retention urinary catheter having an elongate flexible catheter shaft extending between a proximal end and a distal end, a balloon adjacent the distal end, a drainable port distal of the balloon, and a distal tip located distal of the drainable port, and at the proximal end of the catheter shaft a proximal hub with a first port for communication with the balloon and a second port for communication with the drainable port, the improvement comprising:
    the distal tip including a polymer component that is insoluble in urinary fluid in the bladder and which is combined with an eluting component that is dissolvable by urinary fluid and adapted to elute from the distal tip in the presence of urinary fluid in order to increase flexibility of the distal tip.

17. The improvement of claim 16, wherein the eluting component is in the form of particles.

18. The improvement of claim 16, wherein the eluting component comprises salt particles.

\* \* \* \* \*